(12) United States Patent
Li et al.

(10) Patent No.: US 10,883,946 B2
(45) Date of Patent: Jan. 5, 2021

(54) METHOD FOR TESTING PHASE TRANSFORMATION POINT OF ALUMINUM ALLOY

(71) Applicant: CENTRAL SOUTH UNIVERSITY, Hunan (CN)

(72) Inventors: Hongying Li, Hunan (CN); Jiaojiao Liu, Hunan (CN)

(73) Assignee: CENTRAL SOUTH UNIVERSITY, Hunan (CN)

( * ) Notice: Subject to any disclaimer, the term of this patent is extended or adjusted under 35 U.S.C. 154(b) by 137 days.

(21) Appl. No.: 16/079,207

(22) PCT Filed: Mar. 9, 2016

(86) PCT No.: PCT/CN2016/075988
§ 371 (c)(1),
(2) Date: Aug. 23, 2018

(87) PCT Pub. No.: WO2017/152397
PCT Pub. Date: Sep. 14, 2017

(65) Prior Publication Data
US 2019/0094162 A1     Mar. 28, 2019

(51) Int. Cl.
*G01N 25/02*     (2006.01)
*G01K 1/00*     (2006.01)
(Continued)

(52) U.S. Cl.
CPC ............. *G01N 25/12* (2013.01); *G01N 33/20* (2013.01); *C22F 1/002* (2013.01); *C22F 1/04* (2013.01)

(58) Field of Classification Search
USPC ................................... 374/16, 183, 100, 163
See application file for complete search history.

(56) References Cited

U.S. PATENT DOCUMENTS

| 3,953,253 A * | 4/1976 | Clark ..................... C22F 1/006 148/563 |
| 4,166,378 A | 9/1979 | Berger et al. |
| 9,303,303 B2 * | 4/2016 | Meyer ..................... C22F 1/043 |

FOREIGN PATENT DOCUMENTS

| CN | 1651908 A | 8/2005 |
| CN | 101776627 A | 7/2010 |

(Continued)

OTHER PUBLICATIONS

International Search Report issued in connection with International patent application No. PCT/CN2016/075988, Nov. 17, 2016, 4 pages.

*Primary Examiner* — Mirellys Jagan
(74) *Attorney, Agent, or Firm* — Duane Morris LLP

(57) ABSTRACT

A method for testing a phase transformation point of aluminium alloy, comprising cutting an aluminium alloy material to obtain at least three samples to be tested; performing heat treatment on a first sample to be tested to obtain a first resistivity-temperature curve; respectively performing quenching treatment and annealing treatment on a second sample to be tested and a third sample to be tested to obtain the second sample to be tested at a quenched state and the third sample to be tested at a fully annealed state, and respectively heating the second sample to be tested at a quenched state and the third sample to be tested at a fully annealed state to obtain a second resistivity-temperature curve and a third resistivity-temperature curve; obtaining a relative resistivity-temperature curve; and determining a phase transformation starting temperature and a phase transformation termination temperature of the sample to be tested according to the relative resistivity-temperature curve. By means of this method, a phase transformation behavior and a phase transformation temperature under a non-linear cooling condition can be tested. The range of a cooling rate (Continued)

which can be tested in the method is wide, and a phase transformation behavior of a small volume fraction and precipitated phase information about a small size can be captured.

10 Claims, 16 Drawing Sheets

(51) Int. Cl.
*G01K 7/00* (2006.01)
*G01N 25/12* (2006.01)
*G01N 33/20* (2019.01)
*C22F 1/00* (2006.01)
*C22F 1/04* (2006.01)

(56) References Cited

FOREIGN PATENT DOCUMENTS

| CN | 101929967 A | 12/2010 |
| CN | 105044151 A | 11/2015 |
| JP | H09166561 A | 6/1997 |
| WO | 03083462 A | 10/2003 |

\* cited by examiner

METHOD FOR TESTING PHASE TRANSFORMATION POINT OF ALUMINUM ALLOY

CROSS-REFERENCE TO RELATED APPLICATIONS

This application is a U.S. national stage application under 35 U.S.C. § 371 of International Application No. PCT/CN2016/075988, filed Mar. 9, 2016, the entirety of which is incorporated herein by reference.

TECHNICAL FIELD

The present disclosure relates to the field of physical testing of metal materials, and in particular to a method for testing the phase transformation point of an aluminum alloy.

BACKGROUND ART

In the heat treatment process of an aluminum alloy, the solid phase transformation behavior in the cooling process has a great influence on the mechanical properties, corrosion resistance and processing properties of the aluminum alloy. Therefore, accurate measurement of phase transformation temperature has important theoretical significance and engineering value.

Temperature and time are the key factors that determine the solid phase transformation of an aluminum alloy. The cooling curve (temperature-time curve) of an aluminum alloy workpiece in actual production is non-linear, and the corresponding phase transformation process is very complicated; and the cooling rate involved in the heat treatment process of an aluminum alloy has a wide range, for example, the cooling rate of quenching is usually more than 1000° C./min. Furnace cooling is usually employed in homogenization or annealing, which has a very low cooling rate. Under conditions of high cooling rate, the phase transformation of an aluminum alloy has a low volume fraction, and the precipitated phase has uneven distribution and a small size. The commonly used differential scanning calorimetry (DSC) is only suitable for testing the phase transformation behavior occurring under constant temperature or linear cooling conditions, it has narrow testable cooling rate range (about 5-475° C./min) and it is easy to form impurity peaks, furthermore, for the phase transformation behavior with small volume fraction and the precipitated phase with small size, it has low sensitivity, thereby it is difficult to form clear phase transformation peaks.

SUMMARY

The main object of the present disclosure is to provide a method for testing the phase transformation point of an aluminum alloy, which can realize the test for the phase transformation behavior occurring under a non-linear cooling condition and the phase transformation temperature. The method has a wide range of cooling rate and can capture the phase transformation behavior with small volume fraction and the information of precipitated phase with small size.

The present disclosure adopts the following technical solutions:

cutting an aluminum alloy material to be tested according to the preset size to obtain at least three samples to be tested;

performing heat treatment on the first sample to be tested to obtain a first resistivity-temperature curve of the first sample to be tested during the cooling process of the heat treatment;

performing quenching treatment and annealing treatment on the second sample to be tested and the third sample to be tested, respectively, to obtain an as-quenched second sample to be tested and a fully as-annealed third sample to be tested which are then heated, respectively, to obtain a second resistivity-temperature curve and a third resistivity-temperature curve;

obtaining the relative resistivity-temperature curve according to the following formula:

$$\rho_e = \frac{\rho_{AQ}(T) - \rho_i(T)}{\rho_{AQ}(T) - \rho_{FA}(T)},$$

wherein $\rho_{AQ}^{(T)}$ is the resistivity at temperature T of the as-quenched second sample to be tested which is obtained according to the second resistivity-temperature curve; $\rho_{FA}^{(T)}$ is the resistivity at temperature T of the fully as-annealed third sample to be tested which is obtained according to the third resistivity-temperature curve; and $\rho_i^{(T)}$ is the resistivity at temperature T of the first sample to be tested during the heat treatment which is obtained according to the first resistivity-temperature curve;

and determining the phase transformation starting temperature and the phase transformation termination temperature of the sample to be tested according to the relative resistivity-temperature curve.

Further, determining the phase transformation starting temperature and the phase transformation termination temperature of the sample to be tested according to the relative resistivity-temperature curve can include:

determining the extrapolated starting baseline and the extrapolated termination baseline on the relative resistivity-temperature curve, respectively;

defining the temperature corresponding to the intersection point between the straight line where the extrapolated starting baseline is located and the relative resistivity-temperature curve as the phase transformation starting temperature;

and defining the temperature corresponding to the intersection point between the straight line where the extrapolated termination baseline is located and the relative resistivity-temperature curve as the phase transformation termination temperature.

Further, the heat treatment is solid solution, homogenization, annealing or aging.

Further, after performing heat treatment on the first sample to be tested, the method further includes: obtaining a temperature-time curve of the first sample to be tested during the cooling process of the heat treatment.

Further, performing quenching treatment and annealing treatment on the second sample to be tested and the third sample to be tested, respectively, to obtain an as-quenched second sample to be tested and a fully as-annealed third sample to be tested can include:

heating and keeping warm of the second sample to be tested and the third sample to be tested, respectively, so that the soluble phases in the second sample to be tested and the third sample to be tested are fully dissolved into the matrix, and then cooling by way of water quenching, to obtain an as-quenched second sample to be tested and an as-quenched third sample to be tested, respectively;

annealing the as-quenched third sample to be tested at a preset temperature so that the third sample to be tested has the minimum resistivity and hardness, and a fully as-annealed third sample to be tested is obtained;

wherein, the resistivity of the as-quenched second sample to be tested has a theoretical maximum value; and the resistivity of the fully as-annealed third sample to be tested has a theoretical minimum value.

Further, when performing heat treatment on the as-quenched second sample to be tested and the fully as-annealed third sample to be tested, the heating rates of the as-quenched second sample to be tested and the fully as-annealed third sample to be tested are all above 1000° C./min, and both the as-quenched second sample to be tested and the fully as-annealed third sample to be tested have no phase transformation.

Further, during the cooling process of heat treatment, the first sample to be tested is cooled by means of air mist cooling, high pressure gas cooling, air blast cooling, air cooling or furnace cooling.

Further, during the cooling process of heat treatment, the first sample to be tested is cooled at a preset distance from the heat source.

Further, during the cooling process of heat treatment, the average cooling rate of the first sample to be tested is between 2.58° C./min and 1240° C./min.

The principle of the present technical solution is: in the present disclosure, the resistivity of the aluminum alloy is composed of three parts: the resistivity of the aluminum matrix, the resistivity produced by the solid-solution state alloy elements, and the resistivity of the precipitated second phase. According to the calculation formula $$\rho_e = \frac{\rho_{AQ}(T) - \rho_i(T)}{\rho_{AQ}(T) - \rho_{FA}(T)}$$

for the relative resistivity, it is known that the relative resistivity removes the resistivity of the aluminum matrix and can directly reflect the phase transformation behavior of the aluminum alloy.

A method for testing the phase transformation point of an aluminum alloy provided by the present disclosure can realize the test for the phase transformation behavior occurring under a non-linear cooling condition and the phase transformation temperature, can test the phase transformation behavior of an aluminum alloy in a wide range of cooling rate, and can capture the phase transformation behavior with small volume fraction and the information of precipitated phase with small size by means of obtaining resistivity-temperature curve of the first sample to be tested during the heat treatment, the resistivity-temperature curve of the as-quenched second sample to be tested, and the resistivity-temperature curve of the fully as-annealed third sample to be tested to obtain the relative resistivity-temperature curve according to the formula, with the relative resistivity-temperature curve the phase transformation starting temperature and the phase transformation termination temperature of the sample to be tested are obtained. The method also can achieve accuracy measurement.

BRIEF DESCRIPTION OF THE DRAWINGS

In order to more clearly explain the technical solutions of the present disclosure, the drawings needed to be used in the description of the examples will be briefly described below. Of course, the drawings in the following description are merely some examples of the present disclosure, for those having ordinary skills in the art, modifications and substitutions to these drawings may also be made without any creative work.

DETAILED DESCRIPTION

The technical solutions of the present disclosure will be clearly and completely described below with reference to the accompanying drawings. Obviously, the described examples are merely a part of examples of the present disclosure, rather than all examples thereof, and are intended to illustrate the principles of the present disclosure rather than limiting the present disclosure thereto. All other examples obtained by those having ordinary skills in the art without making creative work based on the examples in the present disclosure are within the protection scope of the present disclosure.

Example 1

Table 1 shows the chemical components of the aluminum alloy to be tested which is selected in this example. The chemical components of the aluminum alloy to be tested are as shown in Table 1, in which aluminum is the balance.

TABLE 1

| alloy element(s) | Cu | Fe | Si | Al |
|---|---|---|---|---|
| mass fraction (wt. %) | 4.0 | 0.10 | 0.195 | Bal. |

The method for testing the phase transformation point of an aluminum alloy provided by this example includes the following specific steps:

Step 1: cutting an aluminum alloy material to be tested to obtain at least three samples to be tested, wherein the size of the sample to be tested was 200×5×1 mm, and the precision was controlled within 0.02 mm.

Figure 1:
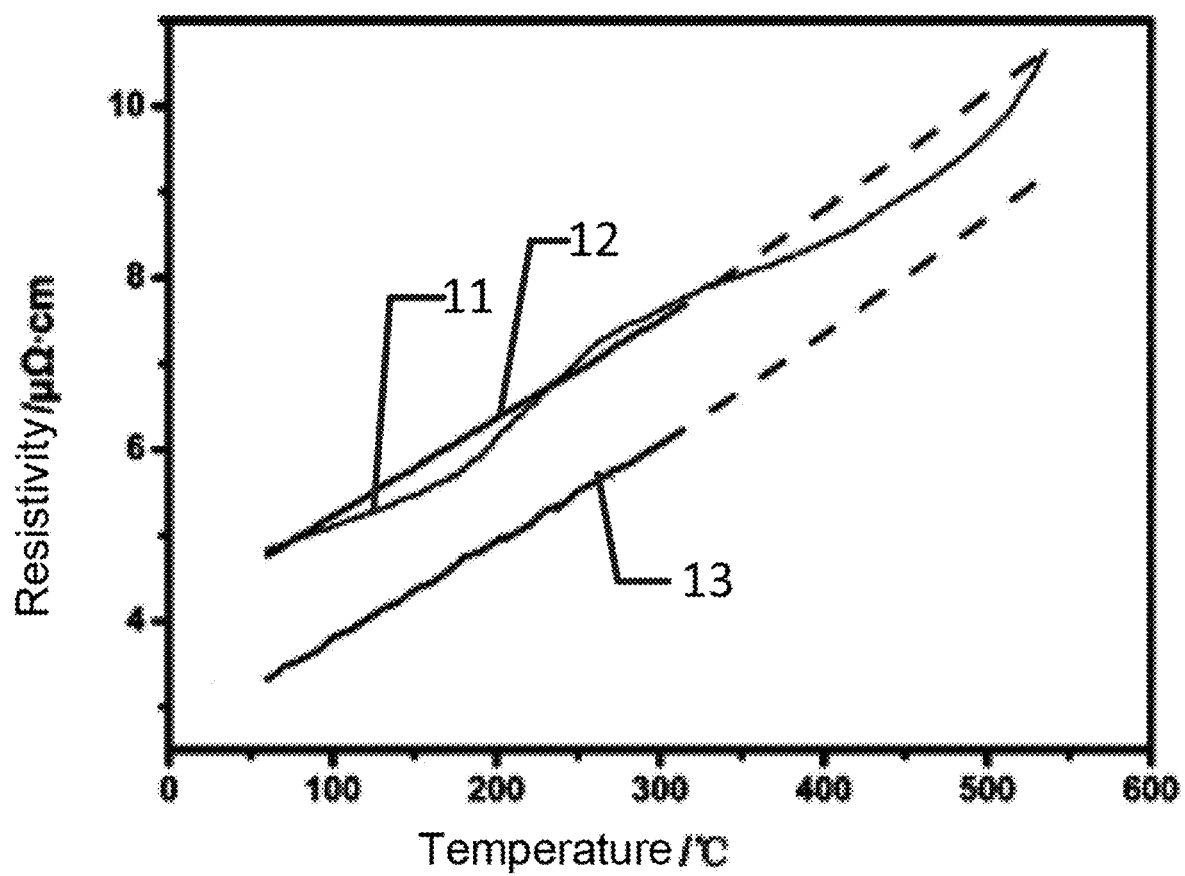
FIG. 1 is a diagram showing the relationship between the resistivity and the temperature provided by Example 1 of the present disclosure.
Figure 2:
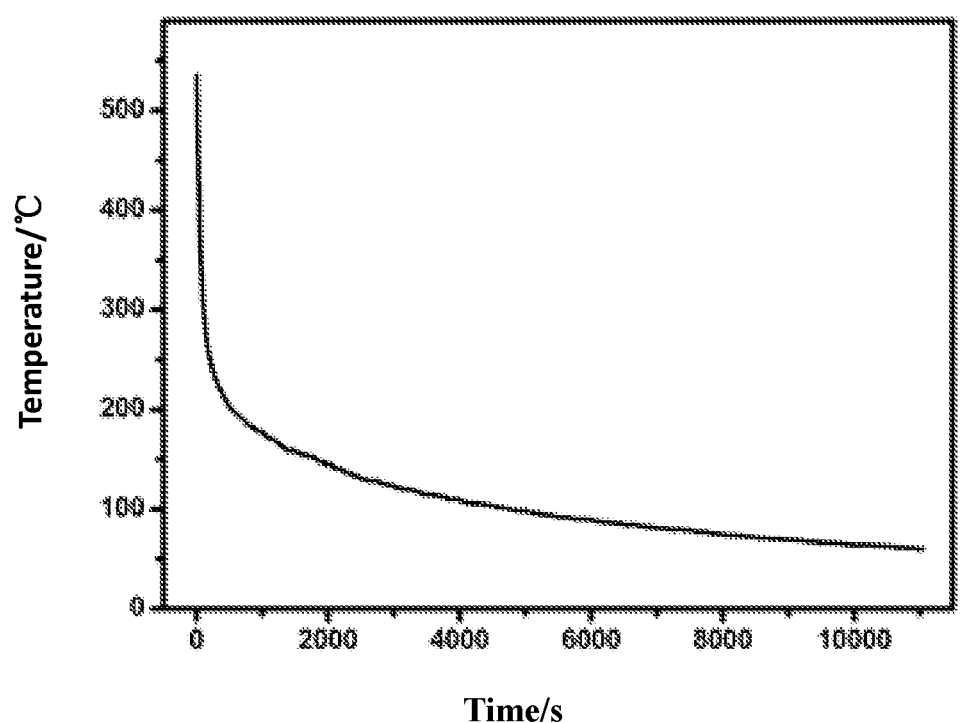
FIG. 2 is a temperature-time curve provided by Example 1 of the present disclosure.

Step 2: After the solid solution and thermal insulation of the first sample to be tested at 535° C. for 2 hours, placing the first sample to be tested at a distance of 30 cm from the door of the heating furnace for cooling (the cooling of the first sample to be tested was affected by the heat radiation in the heating furnace, and the first sample to be tested can also be placed in other heat sources for solid solution and thermal insulation), a first resistivity-temperature curve of the first sample to be tested through a four-probe test method was obtained during the cooling process, and the temperature-time curve (cooling curve) of the first sample to be tested was obtained as well. Wherein, FIG. 1 is a diagram showing the relationship between the resistivity and the temperature provided by Example 1 of the present disclosure, as shown in FIG. 1, 11 is a first resistivity-temperature curve. FIG. 2 is a temperature-time curve provided by Example 1 of the present disclosure, as shown in FIG. 2, the temperature-time curve is nonlinear, and an average cooling rate of 2.58° C./min can be calculated through the data corresponding to this curve.

In this example, the first sample to be tested can also be cooled at other distances from the door of the heating furnace. The resistivity was tested by means of forming an ohmic connection between the equidistant four probes and the surface of the first sample to be tested, then powering a low current on the two external probes with a constant current source, followed by measuring the voltage between the two internal probes with a precision voltmeter. A temperature sensor contacted with the first sample to be tested for obtaining the temperature signal of the first sample to be tested. The voltage value obtained from the precision voltmeter and the temperature signal obtained from the temperature sensor were input into the computer, and the resistivity of the first sample to be tested can be calculated by the voltage value and the preset formula. A first resistivity-temperature curve can be plotted based on the calculated resistivity and the temperature data in the computer, and the computer can record the time information for obtaining the temperature signal. Therefore, the computer can automatically plot the temperature-time curve through the temperature data and the time information.

Step 3: performing quenching treatment and annealing treatment on the second sample to be tested and the third sample to be tested, respectively, i.e., heating and keeping warm of the second sample to be tested and the third sample to be tested, respectively, so that the soluble phases in the second sample to be tested and the third sample to be tested were fully dissolved into the aluminum matrix, afterwards, cooling by water quenching to obtain an as-quenched second sample to be tested and the an as-quenched third sample to be tested. The as-quenched third sample to be tested was annealed at a preset temperature so that the third sample to be tested had the minimum resistivity and hardness, and a fully as-annealed third sample to be tested was obtained; then heating the as-quenched second sample to be tested and the fully annealed third test sample to be tested to 535° C. at a heating rate of 1000° C./min to obtain a second resistivity-temperature curve and a third resistivity-temperature curve, i.e., the resistivity-temperature curve of the as-quenched second sample to be tested and the resistivity-temperature curve of the fully as-annealed third sample to be tested. As shown in FIG. 1, 12 is the resistivity-temperature curve of the second sample to be tested, 13 is the resistivity-temperature curve of the third sample to be tested, wherein the solid line sections of the resistivity-temperature curves of the second sample to be tested and the third sample to be tested were obtained through experimental tests.

In this example, the preset temperatures for quenching and annealing of the samples to be tested with different components are different, and the preset temperatures can be obtained according to the properties of the samples to be tested. The resistivity of the as-quenched second sample to be tested is the theoretical maximum value; and the resistivity of the fully as-annealed third sample to be tested is the theoretical minimum value.

Step 4: obtaining the relative resistivity-temperature curve according to the following formula:

$$\rho_e = \frac{\rho_{AQ}(T) - \rho_i(T)}{\rho_{AQ}(T) - \rho_{FA}(T)},$$

wherein, $\rho_{AQ}^{(T)}$ is the resistivity at temperature T of the as-quenched second sample to be tested which is obtained according to the second resistivity-temperature curve; $\rho_{FA}^{(T)}$ is the resistivity at temperature T of the fully as-annealed third sample to be tested which is obtained according to the third resistivity-temperature curve, and $\rho_i^{(T)}$ is the resistivity at temperature T of the first sample to be tested during the heat treatment which is obtained according to the first resistivity-temperature curve; in this example, the resistivity of the aluminum alloy is composed of three parts: the resistivity of the aluminum matrix, the resistivity produced by the solid-solution state alloy elements, and the resistivity of the precipitated second phase. According to the calculation formula $$\rho_e = \frac{\rho_{AQ}(T) - \rho_i(T)}{\rho_{AQ}(T) - \rho_{FA}(T)}$$

for the relative resistivity described above, the relative resistivity removes the resistivity of the aluminum matrix and can directly reflect the phase transformation behavior of the aluminum alloy.

Figure 3:
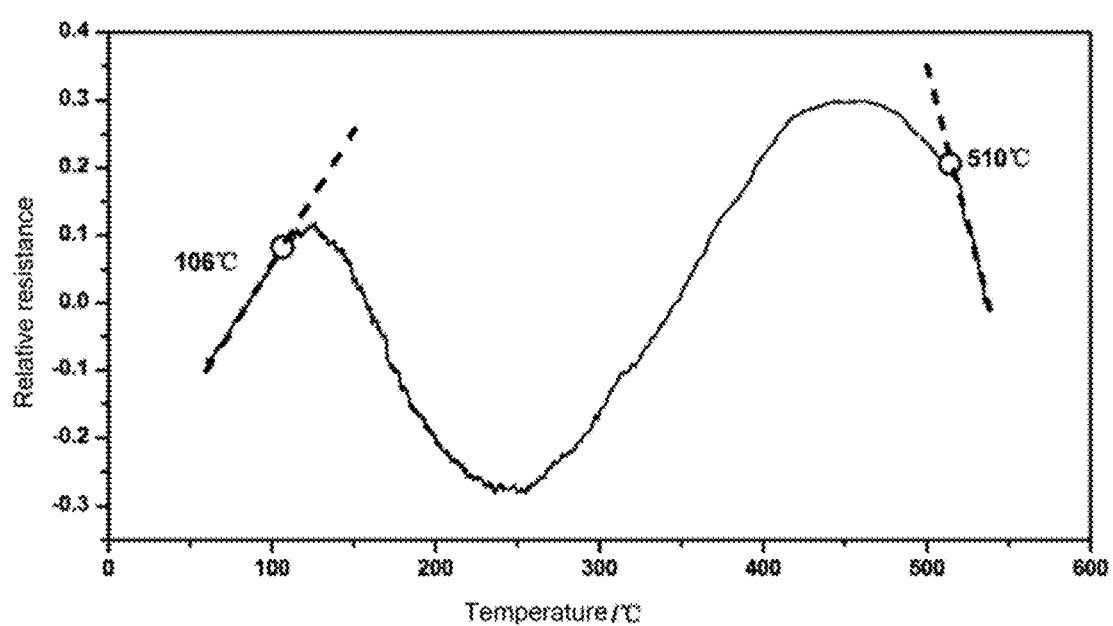
FIG. 3 is a relative resistivity-temperature curve of a first sample to be tested provided by Example 1 of the present disclosure.

In this example, on the second resistivity-temperature curve, the data of the resistivity corresponding to temperature T is $\rho_{AQ}^{(T)}$, and on the third resistivity-temperature curve, the resistivity corresponding to temperature T is $\rho_{FA}^{(T)}$; and on the first resistivity-temperature curve, the resistivity corresponding to temperature T is $\rho_i^{(T)}$. Since the temperature T is a variable, when the temperature T is changed, multiple groups of $\rho_{AQ}^{(T)}$, $\rho_{FA}^{(T)}$ and $\rho_i^{(T)}$ can be obtained, according to the obtained data of $\rho_{AQ}^{(T)}$, $\rho_{FA}^{(T)}$ and $\rho_i^{(T)}$, data of relative resistivity at different temperatures can be calculated according to formula $$\rho_e = \frac{\rho_{AQ}(T) - \rho_i(T)}{\rho_{AQ}(T) - \rho_{FA}(T)},$$

and a relative resistivity-temperature curve can be plotted by taking the temperature T as X-axis and the relative resistivity as Y-axis. The plotted relative resistivity-temperature curve has no impurity peaks. FIG. 3 is a relative resistivity-temperature curve provided by Example 1 of the present disclosure. As shown in FIG. 3, during the cooling process of the aluminum alloy (a first sample to be tested), the relative resistivity varies with the temperature. During the cooling process, an aluminum alloy shows a linear relationship between the relative resistivity and the temperature at the beginning; when the phase transformation occurs, the relative resistivity-temperature curve deviates from the extrapolated starting baseline, and the deviation point represents the phase transformation starting temperature; after the phase transformation is completed, the relative resistivity and the temperature regresses a linear relationship, the relative resistivity-temperature curve coincides with the extrapolated termination baseline, and the regression point is the phase transformation termination temperature. Wherein, the extrapolated starting baseline is the linear part whose slope is not changed between the beginning position and the first phase transformation peak on the relative resistivity-temperature curve, and the extrapolated termination baseline is the linear part whose slope is not changed between the last phase transformation peak and the terminal position on the relative resistivity-temperature curve.

During the cooling process of an aluminum alloy, when the size of the precipitated second phase is close to the mean free path of electrons, there will be strong coherent scattering on electrons, resulting in a significant increase in the resistivity of the aluminum alloy. Therefore, in a non-linear rapid cooling, condition, when the second phase has low volume fraction and/or small size, it will also produce significant resistance response signals. As shown in FIG. 3, at the beginning, when the size of the precipitated second phase is smaller than the mean free path of electrons, the resistivity of the aluminum alloy increases as the size of the second phase increases, but the relative resistivity decreases, and the excited phase transformation peak protrudes upward. When the size of the second phase is equal to the mean free path of electrons, the aluminum alloy has the maximum resistivity and the minimum relative resistivity. When the size of the second phase is greater than the mean free path of electrons, the resistivity of the aluminum alloy decreases as the size of the second phase increases, but the relative resistivity increases, so that the excited phase transformation peak recesses downward.

Step 5: determining the phase transformation starting temperature and the phase transformation termination temperature of the sample to be tested according to the relative resistivity-temperature curve.

In this example, the method for determining the phase transformation starting temperature and the phase transformation termination temperature includes the following specific steps: determining the extrapolated starting baseline and the extrapolated termination baseline on the relative resistivity-temperature curve, and defining the temperature corresponding to the intersection point of the straight line where the extrapolated starting baseline is located with the relative resistivity-temperature curve as the phase transformation starting temperature; and defining the temperature corresponding to the intersection point of the straight line where the extrapolated termination baseline is located and the relative resistivity-temperature curve as the phase transformation termination temperature.

Figure 4:
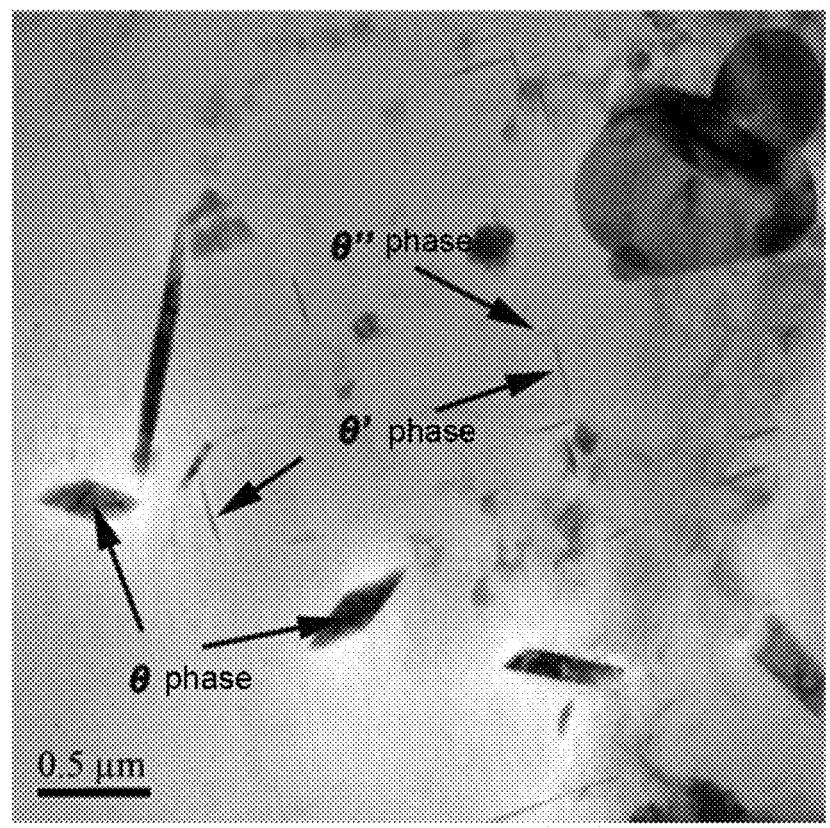
FIG. 4 is the microscopic structure picture of a first sample to be tested after phase transformation provided by Example 1 of the present disclosure.

In this example, as shown in FIG. 3, the phase transformation starting temperature is 510° C., and the phase transformation termination temperature is 106° C. There are a total of 3 phase transformation peaks on the relative resistivity-temperature curve, indicating that a total of three kinds of phase transformations had occurred for the first sample to be tested and three kinds of second phases were precipitated. FIG. 4 is the microscopic structure picture of a first sample to be tested after phase transformation provided by Example 1. As shown in FIG. 4, the first sample to be tested has a total of three phases in its structure, i.e., θ phase, θ' phase and θ" phase, respectively. Wherein, the three phase transformation peaks on the relative resistivity-temperature curve in FIG. 3 correspond to the θ phase, θ' phase and θ" phase in FIG. 4, respectively. As shown in FIG. 4, the bulky massive particles having no phase relationship with the matrix is a θ phase, the acicular phase of 300 nm or more and parallel to the $\{001\}_{Al}$ direction is a θ' phase, and the acicular phase of 100-150 nm is a θ" phase. Therefore, the actual occurring phase transformation of the first sample to be tested and the result of the phase transformation reflected on the relative resistivity-temperature curve are the same. Therefore, the phase transformation starting temperature and the phase transformation termination temperature can be determined by the relative resistivity-temperature curve.

On the basis of the above example, when it is required to perform multiple phase transformation tests on the aluminum alloy to be tested, it is necessary to cut the aluminum alloy into at least two samples to be tested for respective heat treatment, and at least two first resistivity-temperature curves are obtained. However, since the resistivity-temperature curve of the as-quenched second sample to be tested and the resistivity-temperature curve of the fully as-annealed third sample to be tested will be served as the reference curve, there is no need for reacquisition. Along with the obtained at least two first resistivity-temperature curves, at least two relative resistivity-temperature curves are determined, respectively, thereby to determine the phase transformation starting temperature and the phase transformation termination temperature.

Example 2

The differences between Example 2 and Example 1 lie in that: 1) chemical components of the selected aluminum alloy to be tested are different. Table 2 shows the chemical components of the aluminum alloy to be tested which is selected in this example. The chemical components of the aluminum alloy to be tested are as shown in Table 2.

TABLE 2

| | alloy element(s) | | | | | | | |
|---|---|---|---|---|---|---|---|---|
| | Mg | Zn | Fe | Si | Mn | Zr | Cr | Al |
| mass fraction (wt. %) | 1.19 | 4.37 | 0.17 | 0.11 | 0.15 | 0.14 | 0.11 | Bal. |

2) Cutting size of the aluminum alloy to be tested is different. In the present example, the aluminum alloy to be tested was cut into samples with a size of 150×5×0.8 mm, and the precision was controlled within 0.02 mm. Wherein, the sizes of the first sample to be tested, the second sample to be tested and the third sample to be tested were all the same.

Figure 5:
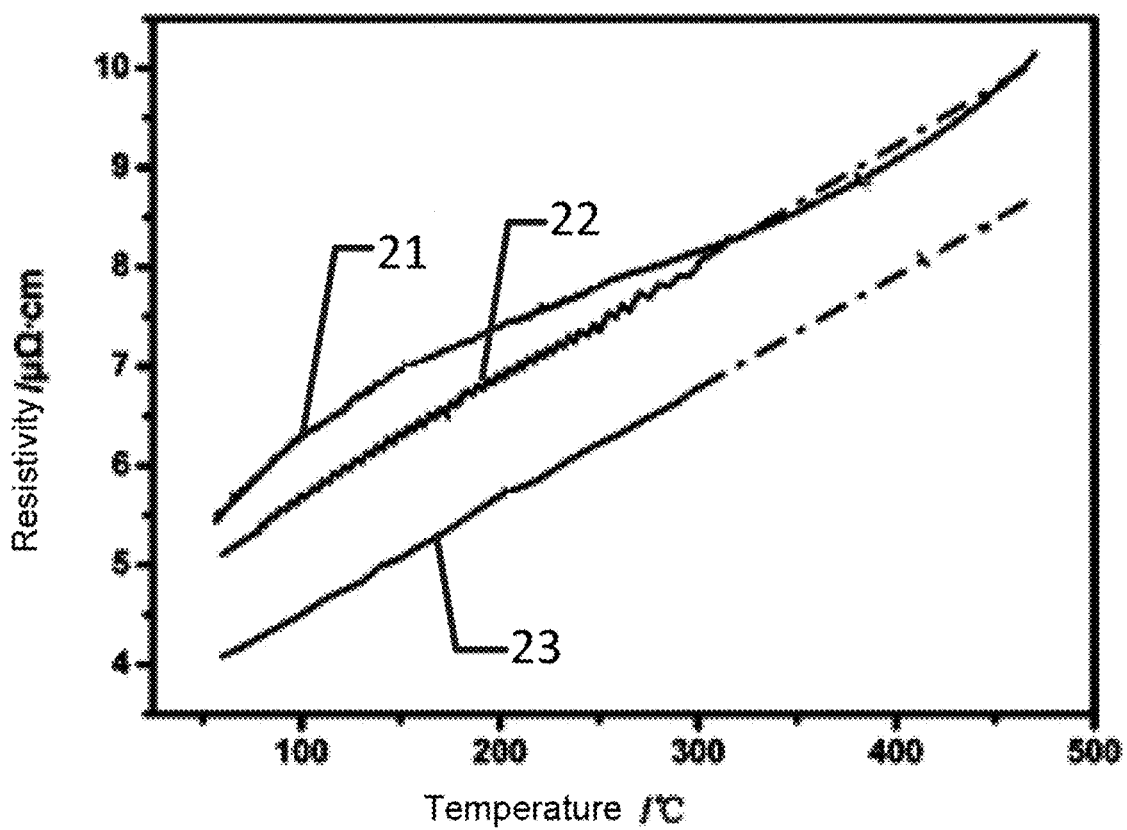
FIG. 5 is a diagram showing the relationship between the resistivity and the temperature provided by Example 2 of the present disclosure.
Figure 6:
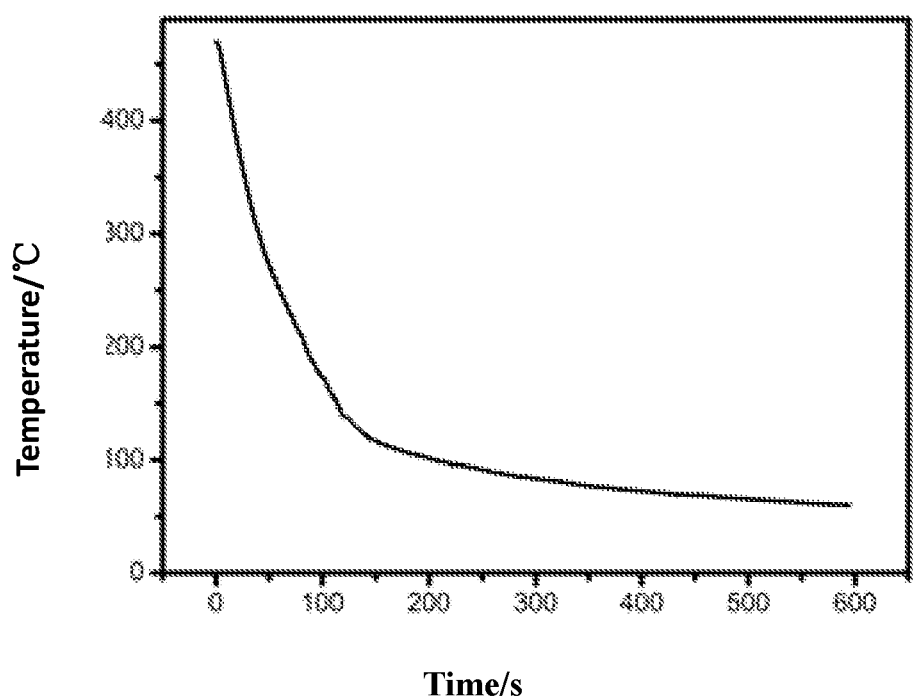
FIG. 6 is a temperature-time curve provided by Example 2 of the present disclosure.

3) The first sample to be tested had different solid solution and thermal insulation and cooling conditions. In this example, the first sample to be tested was air-cooled after solid solution and thermal insulation at 470° C. for 1 hour to obtain a first resistivity-temperature curve and a temperature-time curve, wherein FIG. 5 is a diagram showing the relationship between the resistivity and the temperature provided by Example 2, 21 is the first resistivity-temperature curve. FIG. 6 shows the temperature-time curve provided by Example 2. An average cooling rate of 41.3° C./min of the first sample to be tested can be calculated by the temperature-time curve.

The as-quenched second sample to be tested and the fully as-annealed third sample to be tested had different heating conditions. In this example, the as-quenched second sample to be tested and the fully annealed third test sample to be tested were heated to 470° C. at a heating rate of 1200° C./min, to obtain a second resistivity-temperature curve and a third resistivity-temperature curve which are as shown in FIG. 5, in which 22 is the second resistivity-temperature curve, and 23 is the third resistivity-temperature curve, and both of them have linear relationships.

Figure 7:
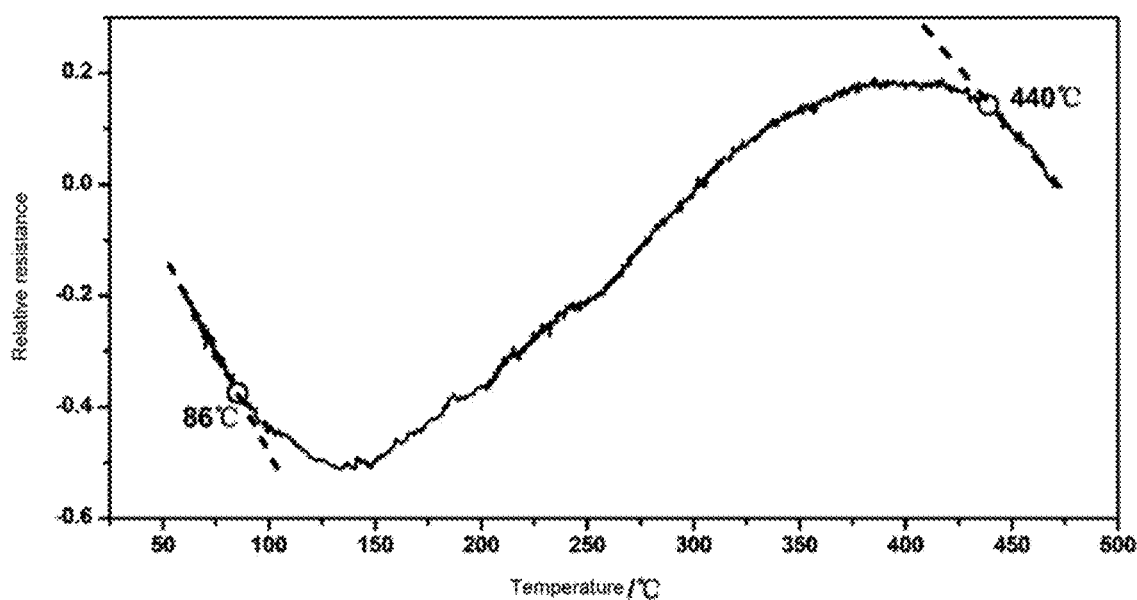
FIG. 7 is a relative resistivity-temperature curve of a first sample to be tested provided by Example 2 of the present disclosure.
Figure 8:
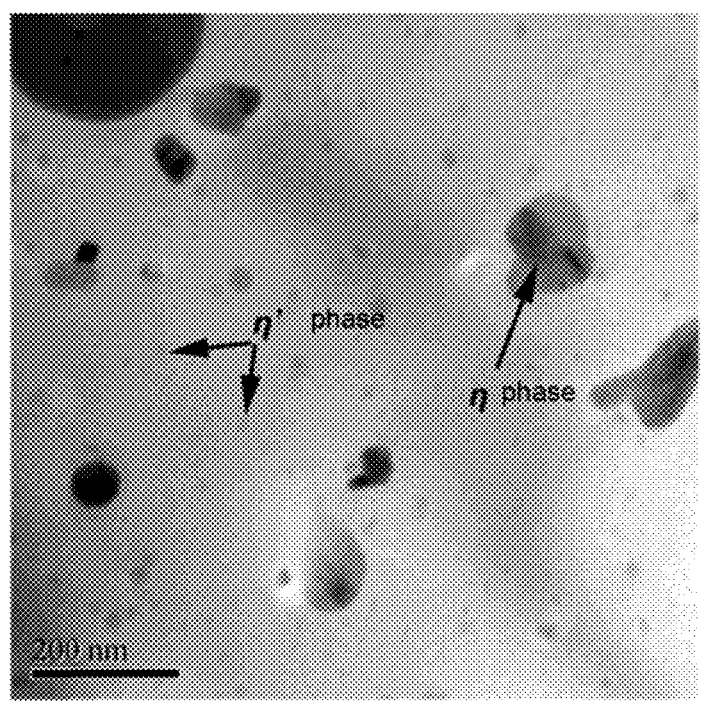
FIG. 8 is the microscopic structure picture of a first sample to be tested after phase transformation provided by Example 2 of the present disclosure.

FIG. 7 is a relative resistivity-temperature curve provided by Example 2. Wherein, the method for obtaining the relative resistivity-temperature curve and the method for obtaining the phase transformation starting temperature and the phase transformation termination temperature were the same as those in Example 1. As shown in FIG. 7, the phase transformation starting temperature and the phase transformation termination temperature for the first sample to be tested were 440° C. and 86° C., respectively, and two phase transformation peaks appeared in the relative resistivity-temperature curve, indicating that two phase transformations had occurred for the first sample to be tested during the cooling process. FIG. 8 is the microscopic structure picture of a first sample to be tested provided by Example 2 that underwent phase transformation after being cooled. As shown in FIG. 8, the η phase is a bulky massive phase, and the η' phase has a small size of 10-30 nm, and the two phase transformation peaks in FIG. 7 correspond to the η phase and the η' phase of the first sample to be tested that underwent phase transformation, respectively. Therefore, the actual occurring phase transformation of the first sample to be tested and the result of the phase transformation reflected on the relative resistivity-temperature curve are the same. Therefore, the phase transformation starting temperature and the phase transformation termination temperature can be determined by the relative resistivity-temperature curve.

Example 3

The differences between Example 3 and Example 1 lie in that: 1) chemical components of the selected aluminum alloy to be tested are different. Table 3 shows the chemical components of the aluminum alloys to be tested which are selected in this example. The chemical components of the aluminum alloys to be tested are as shown in Table 3.

TABLE 3

| | alloy element(s) | | | | | | | |
| --- | --- | --- | --- | --- | --- | --- | --- | --- |
| | Cu | Mg | Zn | Fe | Si | Mn | Zr | Cu | Al |
| mass fraction (wt. %) | 2.37 | 2.15 | 6.1 | 0.15 | 0.12 | 0.09 | 0.1 | 2.37 | Bal. |

Figure 9:
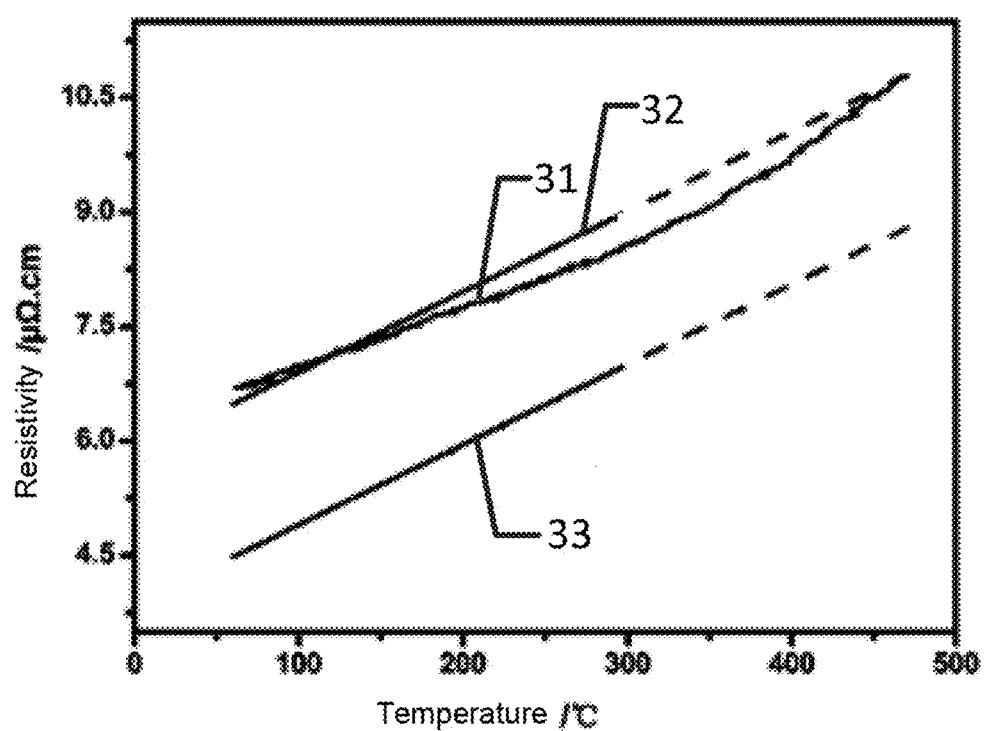
FIG. 9 is a diagram showing the relationship between the resistivity and the temperature provided by Example 3 of the present disclosure.
Figure 10:
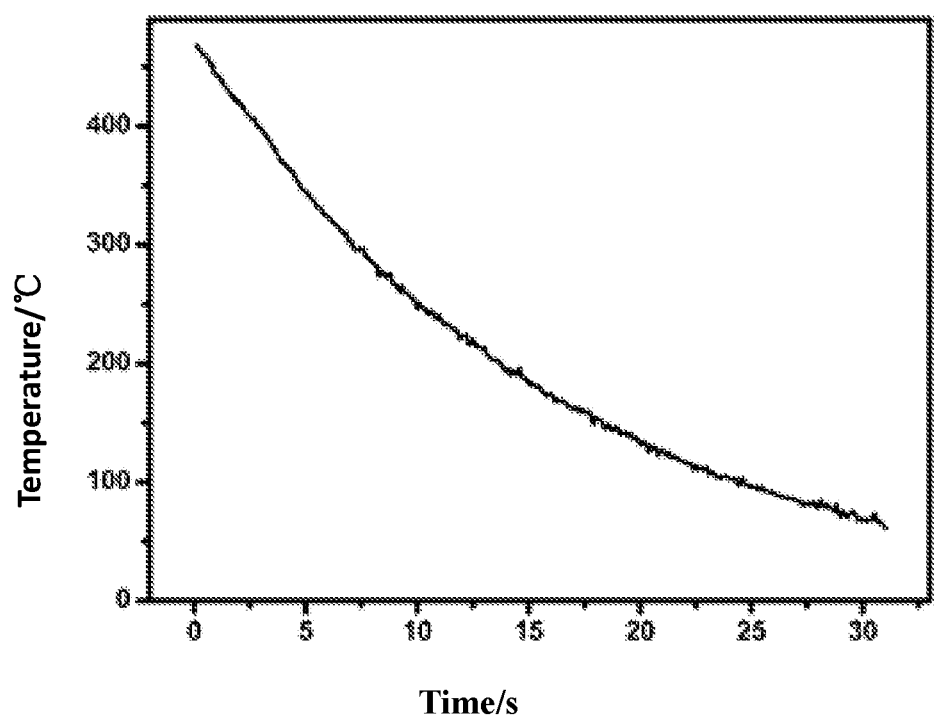
FIG. 10 is a temperature-time curve provided by Example 3 of the present disclosure.

2) The first sample to be tested had different solid solution and thermal insulation and cooling conditions. In this example, the first sample to be tested was high pressure gas cooled after solid solution and thermal insulation at 470° C. for 1 hour to obtain a first resistivity-temperature curve and a temperature-time curve, wherein FIG. 9 is a diagram showing the relationship between the resistivity and the temperature provided by Example 3, 31 is the first resistivity-temperature curve. FIG. 10 shows the temperature-time curve provided by Example 3. An average cooling rate of 768.8° C./min of the first sample to be tested can be calculated by the temperature-time curve.

3) The as-quenched second sample to be tested and the fully as-annealed third sample to be tested had different heating conditions. In this example, the as-quenched second sample to be tested and the fully annealed third test sample to be tested were heated to 470° C. at a heating rate of 1400° C./min, to obtain a second resistivity-temperature curve and a third resistivity-temperature curve, in which the second resistivity-temperature curve and the third resistivity-temperature curve are as shown in FIG. 9, 32 is the second resistivity-temperature curve, and 33 is the third resistivity-temperature curve, and both of them have linear relationship.

Figure 11:
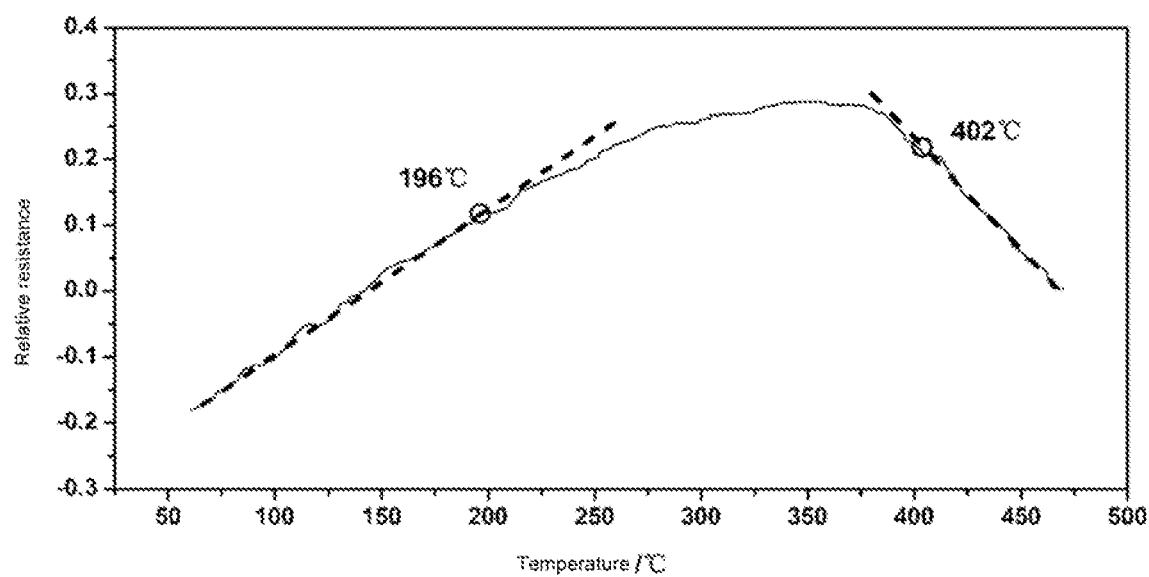
FIG. 11 is a relative resistivity-temperature curve of a first sample to be tested provided by Example 3 of the present disclosure.
Figure 12:
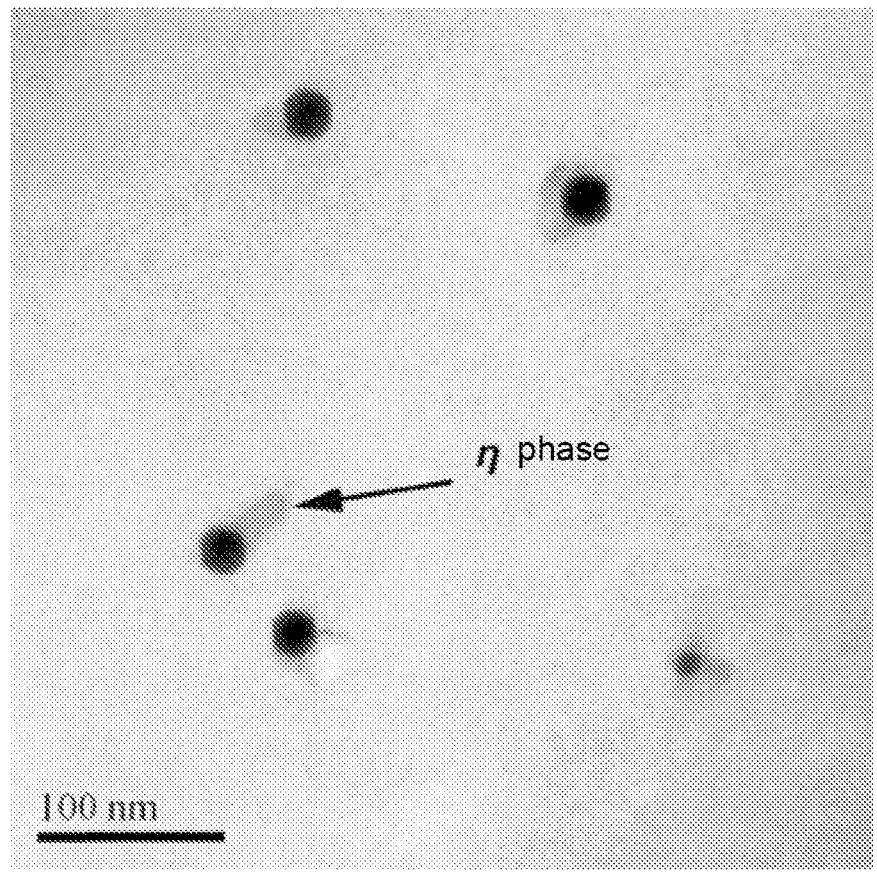
FIG. 12 is the microscopic structure picture of a first sample to be tested after phase transformation provided by Example 3 of the present disclosure.

FIG. 11 is a relative resistivity-temperature curve of a first sample to be tested provided by Example 3 of the present disclosure, wherein, the method for obtaining the relative resistivity-temperature curve and the method for obtaining the phase transformation starting temperature and the phase transformation termination temperature are the same as those in Example 1. As shown in FIG. 11, the phase transformation starting temperature and the phase transformation termination temperature for the first sample to be tested were 402° C. and 196° C., respectively, and one phase transformation peak appeared in the relative resistivity-temperature curve, indicating that one phase transformation had occurred for the first sample to be tested during the cooling process. FIG. 12 is the microscopic structure picture of a first sample to be tested provided by Example 3 that underwent phase transformation after being cooled. As shown in FIG. 12, the η phase forms nucleuses on the $Al_3Zr$ particles with a size of about 30-50 nm, and the one phase transformation peak in FIG. 11 corresponds to the η phase of the sample to be tested that underwent phase transformation. Therefore, the actual occurring phase transformation of the first sample to be tested and the result of the phase transformation reflected on the relative resistivity-temperature curve are the same. Therefore, the phase transformation starting temperature and the phase transformation termination temperature can be determined by the relative resistivity-temperature curve.

Example 4

Figure 13:
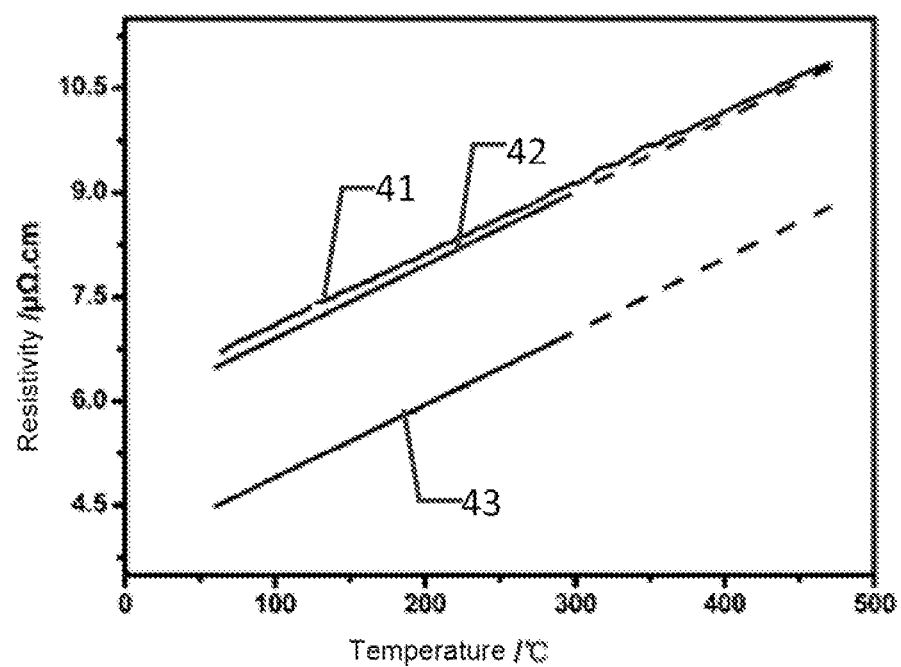
FIG. 13 is a diagram showing the relationship between the resistivity and the temperature provided by Example 4 of the present disclosure.
Figure 14:
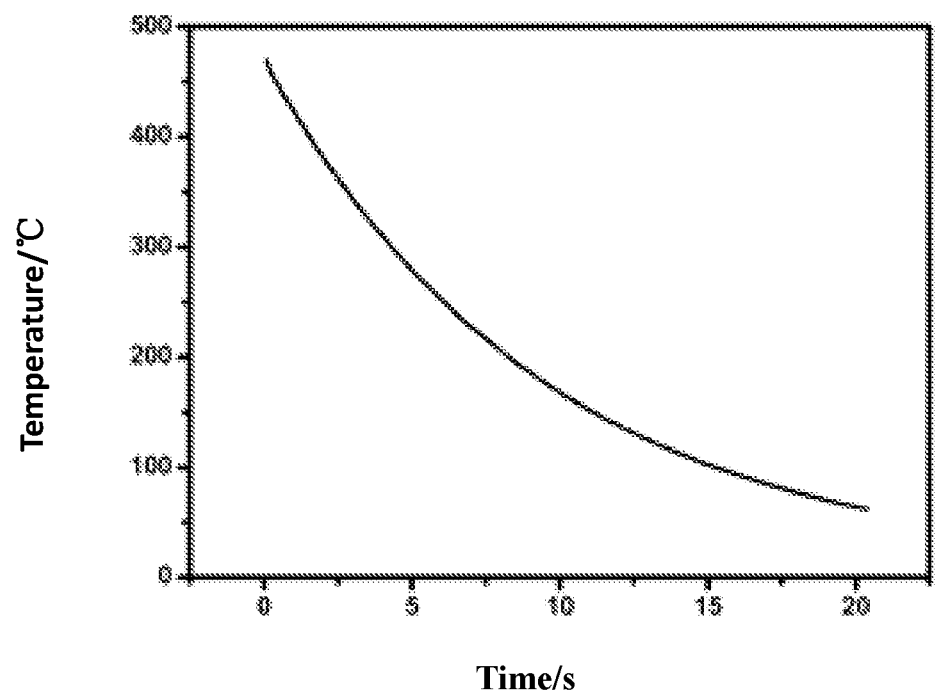
FIG. 14 is a temperature-time curve provided by Example 4 of the present disclosure.

The difference between Example 4 and Example 3 lies in that: the first sample to be tested has different cooling conditions. In this example, the first sample to be tested was air mist cooled after solid solution and thermal insulation at 470° C. for 1 hour to obtain a first resistivity-temperature curve and a temperature-time curve, wherein FIG. 13 is a first resistivity-temperature curve provided by Example 4, and 41 is the first resistivity-temperature curve. FIG. 14 is the temperature-time curve provided by Example 4. As shown in FIG. 14, an average cooling rate of 1240° C./min of the first sample to be tested can be calculated by the temperature-time curve.

In this example, since the second sample to be tested and the third sample to be tested were processed in the same manner as in the third example, the second resistivity-temperature curve and the third resistivity-temperature temperature curve which were the same as those in Example 3 were obtained (as shown in FIG. 13, 42 is the second resistivity-temperature curve of this example, and 43 is the third resistivity-temperature curve of this example, both of them have linear relationship).

Figure 15:
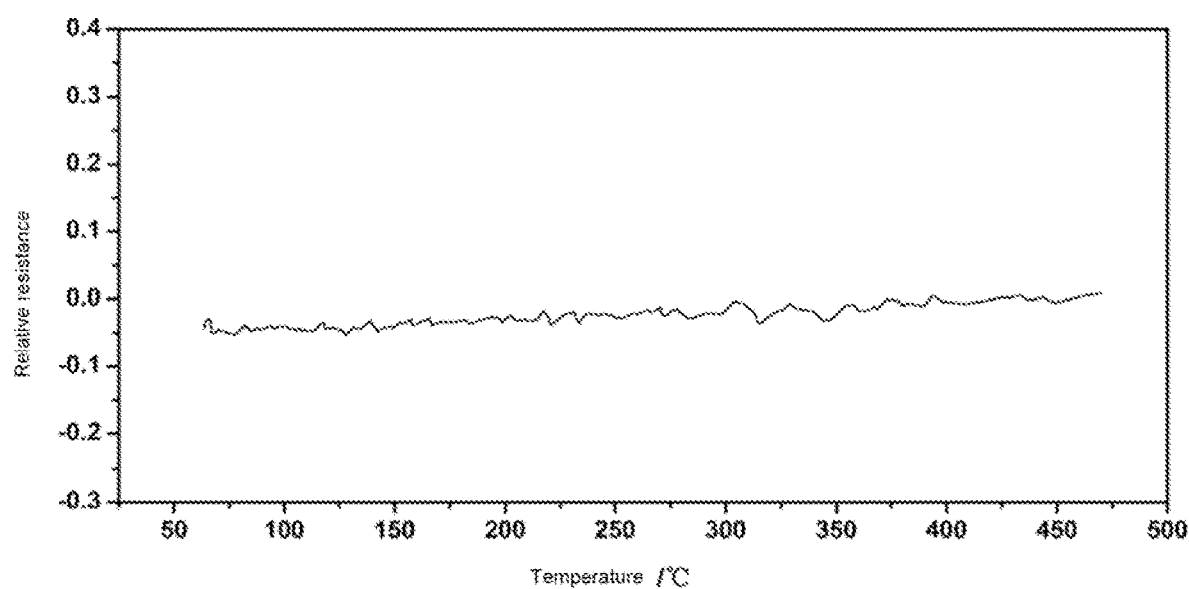
FIG. 15 is a relative resistivity-temperature curve of a first sample to be tested provided by Example 4 of the present disclosure.
Figure 16:
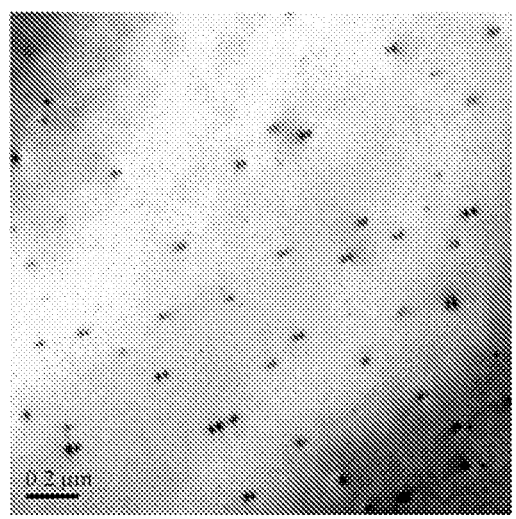
FIG. 16 is the microscopic structure picture of a first sample to be tested after phase transformation provided by Example 4 of the present disclosure.

FIG. 15 is a relative resistivity-temperature curve of a first sample to be tested provided by Example 4. As shown in FIG. 15, since the cooling rate is high, no phase transformation peak appears on the relative resistivity-temperature curve, indicating that there is no second phase precipitated during the cooling process for the first sample to be tested. FIG. 16 is the microscopic structure picture of a first sample to be tested provided by Example 4 that underwent phase transformation after being cooled. As shown in FIG. 16, no η phase is found to be precipitated on $Al_3Zr$ particles. Therefore, the actual occurring phase transformation of the sample to be tested and the result of the phase transformation reflected on the relative resistivity-temperature curve are the same.

It should be noted that although the exemplary example of the present disclosure adopts a solid solution heat treatment method for the first sample to be tested, the heat treatment methods in the examples of the present disclosure are not limited thereto, the first sample to be tested can also be subjected to heat treatments such as homogenization, annealing, or aging, and the like. In the exemplary examples of the present disclosure, cooling methods such as air mist cooling, high pressure gas cooling, and air cooling, etc. were used for the first sample to be tested, however the examples of the present disclosure are not limited thereto, and other cooling methods such as air blast cooling and furnace cooling, etc., can also be used.

The examples described above are merely specific examples of the present disclosure, however the protection scope of the present disclosure is not limited thereto, and any variations or substitutions within the technical scope disclosed by the present disclosure easily conceived by any technical person skilled in the art should be covered by the protection scope of the present disclosure. Therefore, the protection scope of the present disclosure shall be defined by the protection scope of the claims.

The invention claimed is:

1. A method for testing the phase transformation point of an aluminum alloy, wherein it comprises the steps of:
   cutting an aluminum alloy material to be tested according to a preset size to obtain at least three samples to be tested;
   performing heat treatment on a first sample to be tested to obtain a first resistivity-temperature curve of the first sample to be tested during a cooling process of the heat treatment;
   performing quenching treatment and annealing treatment on a second sample to be tested and a third sample to be tested, respectively, to obtain an as-quenched second sample to be tested and a fully as-annealed third sample to be tested, which are then heated, respectively, to obtain a second resistivity-temperature curve and a third resistivity-temperature curve;
   obtaining a relative resistivity-temperature curve according to the following formula:

$$\rho_e = \frac{\rho_{AQ}(T) - \rho_i(T)}{\rho_{AQ}(T) - \rho_{FA}(T)},$$

wherein $\rho_{AQ}^{(T)}$ is the resistivity at temperature T of the as-quenched second sample to be tested which is obtained according to the second resistivity-temperature curve; $\rho_{FA}^{(T)}$ is the resistivity at temperature T of the fully as-annealed third sample to be tested which is obtained according to the third resistivity-temperature curve; and $\rho_i^{(T)}$ is the resistivity at temperature T of the first sample to be tested during the heat treatment which is obtained according to the first resistivity-temperature curve;
   and determining the phase transformation starting temperature and the phase transformation termination temperature of the first, second and third samples to be tested according to the relative resistivity-temperature curve.

2. The method according to claim 1, wherein the step of determining the phase transformation starting temperature and the phase transformation termination temperature of the first, second and third samples to be tested according to the relative resistivity-temperature curve comprises:
   determining an extrapolated starting baseline and an extrapolated termination baseline on the relative resistivity-temperature curve;
   defining a temperature corresponding to the intersection point of the straight line where the extrapolated starting baseline is located with the relative resistivity-temperature curve as the phase transformation starting temperature;
   and defining a temperature corresponding to the intersection point of the straight line where the extrapolated termination baseline is located with the relative resistivity-temperature curve as the phase transformation termination temperature.

3. The method according to claim 1, wherein after performing heat treatment on the first sample to be tested, the method further includes: obtaining a temperature-time curve of the first sample to be tested during the cooling process of the heat treatment.

4. The method according to claim 1, wherein the step of performing quenching treatment and annealing treatment on a second sample to be tested and a third sample to be tested, respectively, to obtain an as-quenched second sample to be tested and a fully as-annealed third sample to be tested includes:
   heating and keeping warm of the second sample to be tested and the third sample to be tested, so that soluble phases in the second sample to be tested and the third sample to be tested are fully dissolved into a matrix, and then cooling by way of water quenching, to obtain an as-quenched second sample to be tested and an as-quenched third sample to be tested;
   annealing the as-quenched third sample to be tested at a preset temperature so that the third sample to be tested has a minimum resistivity and hardness, and a fully as-annealed third sample to be tested is obtained;
   wherein, the resistivity of the as-quenched second sample to be tested is a theoretical maximum value; and the resistivity of the fully as-annealed third sample to be tested is a theoretical minimum value.

5. The method according to claim 1, wherein when performing heat a treatment on the as-quenched second sample to be tested and the fully as-annealed third sample to be tested, the heating rates of the as-quenched second sample to be tested and the fully as-annealed third sample to be tested are all above 1000° C./min, and both the as-quenched second sample to be tested and the fully as-annealed third sample to be tested have no phase transformation.

6. The method according to claim 1, wherein the heat treatment is solid solution, homogenization, annealing or aging.

7. The method according to claim 1, wherein during the cooling process of heat treatment, the first sample to be tested is cooled by means of air mist cooling, high pressure gas cooling, air blast cooling, air cooling or furnace cooling.

8. The method according to claim 1, wherein during the cooling process of heat treatment, the first sample to be tested is cooled at a preset distance from a heat source.

9. The method according to claim 7, wherein during the cooling process of heat treatment, an average cooling rate of the first sample to be tested is between 2.58° C./min and 1240° C./min.

10. The method according to claim 8, wherein during the cooling process of heat treatment, an average cooling rate of the first sample to be tested is between 2.58° C./min and 1240° C./min.

* * * * *